United States Patent [19]

Ismach

[11] 4,141,354
[45] Feb. 27, 1979

[54] VENTILATOR SYSTEM FOR CONTROLLING, ASSISTING AND MONITORING A PATIENT'S BREATHING

[76] Inventor: Aaron Ismach, 200 Upper College Ter., Frederick, Md. 21701

[21] Appl. No.: 774,262

[22] Filed: Mar. 4, 1977

[51] Int. Cl.² .......................................... A61M 16/00
[52] U.S. Cl. ........................ 128/145.6; 128/DIG. 17
[58] Field of Search ............ 128/145.5, 145.6, 145.8, 128/142 R, 142.2, 188, DIG. 17, 202

[56] References Cited

U.S. PATENT DOCUMENTS

| 3,530,856 | 9/1970 | Bird et al. | 128/145.6 |
| 3,730,180 | 5/1973 | Davison | 128/145.6 |
| 3,890,967 | 6/1975 | Elam et al. | 128/202 |
| 3,898,987 | 8/1975 | Elam | 128/145.8 |
| 3,905,362 | 9/1975 | Eyrick et al. | 128/145.6 |
| 3,910,270 | 10/1975 | Stewart | 128/188 X |
| 4,051,847 | 10/1977 | Henkin | 128/145.6 |
| 4,056,099 | 11/1977 | Metivier | 128/145.6 |
| 4,057,059 | 11/1977 | Reid, Jr. et al. | 128/145.8 |

*Primary Examiner*—Henry J. Recla
*Attorney, Agent, or Firm*—Edward H. Loveman

[57] ABSTRACT

A ventilator system for controlling, assisting, and monitoring a patient's breathing comprising a breathing circuit having hoses for delivering breathing gas to a patient and receiving exhaled gas from the patient. Bellows which are axially compressed and expanded by a detachably coupled gas driven piston, pass fresh breathing gas to the patient via an inhalation hose. A pneumatic assist circuit can be set to initiate and maintain inhalation automatically, or under manual control.

9 Claims, 11 Drawing Figures

VENTILATOR SYSTEM FOR CONTROLLING, ASSISTING AND MONITORING A PATIENT'S BREATHING

This invention relates to the art of ventilators and more particularly concerns a ventilator system for controlling, assisting and monitoring a patient's breathing.

The present invention is an improvement over the medical ventilators described in my U.S. Pat. Nos. 3,251,359 and 3,556,095. This invention comprises a novel combination of pneumatic components and pneumatic circuits which achieves great versatility, superior controls, greater assistor sensitivity, a novel highly efficient positive end expiratory pressure valve (PEEP), greater safety, controlled air-oxygen breathing gas, and superior patient breathing circuits.

The new ventilator system is used to either control or assist the breathing of patients especially in emergency situations and involves a rugged portable unit, entirely pneumatic in operation and extremely economical in its driving gas requirements. While having these features, the ventilator does not sacrifice medical utility since it has a full range of controls, conveniently arranged and capable of independent adjustment of all medical parameters. It is constructed for ease in sterilizing the entire patient breathing circuit, and may, by rapid changes of the size of the patient breathing circuit, be employed for pediatric or adult use. The new ventilator is multipurpose in that it is capable of convenient use throughout the hospital as well as in an ambulance during transport.

It is, therefore, the primary object of the present invention to provide an emergency volume cycled ventilator which is light in weight, rugged, small in size, and economical in driving power requirements, so that it is truly portable and capable of being used in emergency vehicles, easily transported with the patient in the vehicle without interfering with access of the medical team to the patient, easily moved with the patient from the vehicle into the hospital emergency room and other areas so that it is possible to maintain safe, effective ventilation at all times.

Another object of the present invention is to provide the operator with convenient meaningful independent controls for setting the following major ventilation parameters:

(1) Volume, liters of breathing gas delivered to the patient
(2) Percent Oxygen in the air-oxygen mixture delivered to the patient
(3) Breathing rate, breaths per minute, and
(4) Inspiratory flow rate, liters/sec. The controls are completely independent so that changing one does not affect or require resetting of the other paramters, which is an important consideration if the ventilator is to be used by a semi-skilled operator under the general (perhaps remote) supervision of a trained medical practitioner.

Another object of the present invention is to provide the ventilator with various modes of operation which are selectable at the option of the operator i.e. as (1) a controller, whereby the patient is forced to breath in unison with the device in accordance with a predetermined breathing pattern; as (2) an assistor, whereby the patient triggers the start of inspiration any time during the cycle, and as (3) an assistor-controller, whereby if the patient fails to initiate the trigger to start inspiration, the device does so automatically after the expiration of a given time; or (4) as a ventilator wherein the operator can manually induce inspiration at any time that he desires.

Another object of the present invention is to provide easily removable patient breathing circuits permitting sterilization between uses and use of patient breathing circuits of various capacities, to match the capacity of the recipient i.e. adult, child, or infant. Each patient breathing circuit is complete with its own bellows, inlet and outlet valves, air-oxygen concentration valve, pressure safety valve, and pressure operated expiratory valve. If employed as an anesthesia ventilator, a spill valve is added. Bacterial filters may be added on the breathing gas inlet and the patient exhalation ports. A spirometer or a ventilation meter can be connected to the exhalation port to monitor exhaled gas volume. For long time ventilation, a humidifier may be added to the patient breathing circuit to humidify the breathing gas prior to delivery to the patient.

Another object of the present invention is to provide a positive end expiratory pressure (PEEP) valve that is isolated from the patient, hence avoiding contamination and the requirement for sterilization between patients, and which during exhalation provides a true shift of the reference pressure axis from a zero value to a selected predetermined value, without distortion of exhalation pressure and flow traces, by providing a completely passive non-resistant path for patient exhalation until the exhalation gas pressure drops to the predetermined positive value when an infinite resistance is encountered. This is in contrast to conventional spring biased PEEP valves directly located in the patient breathing circuit, which can easily be contaminated and which, due to throttling of the exhaled gas flow, harmfully distort the exhalation flow and pressure traces, leading to inefficient ventilation.

Still another object of the present invention is to provide a ventilator with a pressure sensing device in the patient breathing circuit which when connected to an accessory alarm module produces an audible alarm in the event that the patient is accidentally disconnected from the ventilator or if the ventilator stops cycling.

These and other objects and many of the attendant advantages of this invention will be readily appreciated as the same becomes better understood by reference to the following detailed description when considered in connection with the accompanying drawing in which:

In the following description the replaceable and inter-changeable patient breathing circuit associated with the ventilator is also referred to as the "patient circuit" and "PEEP is an acronym used for "positive end expiratory pressure".

Figure 1A:
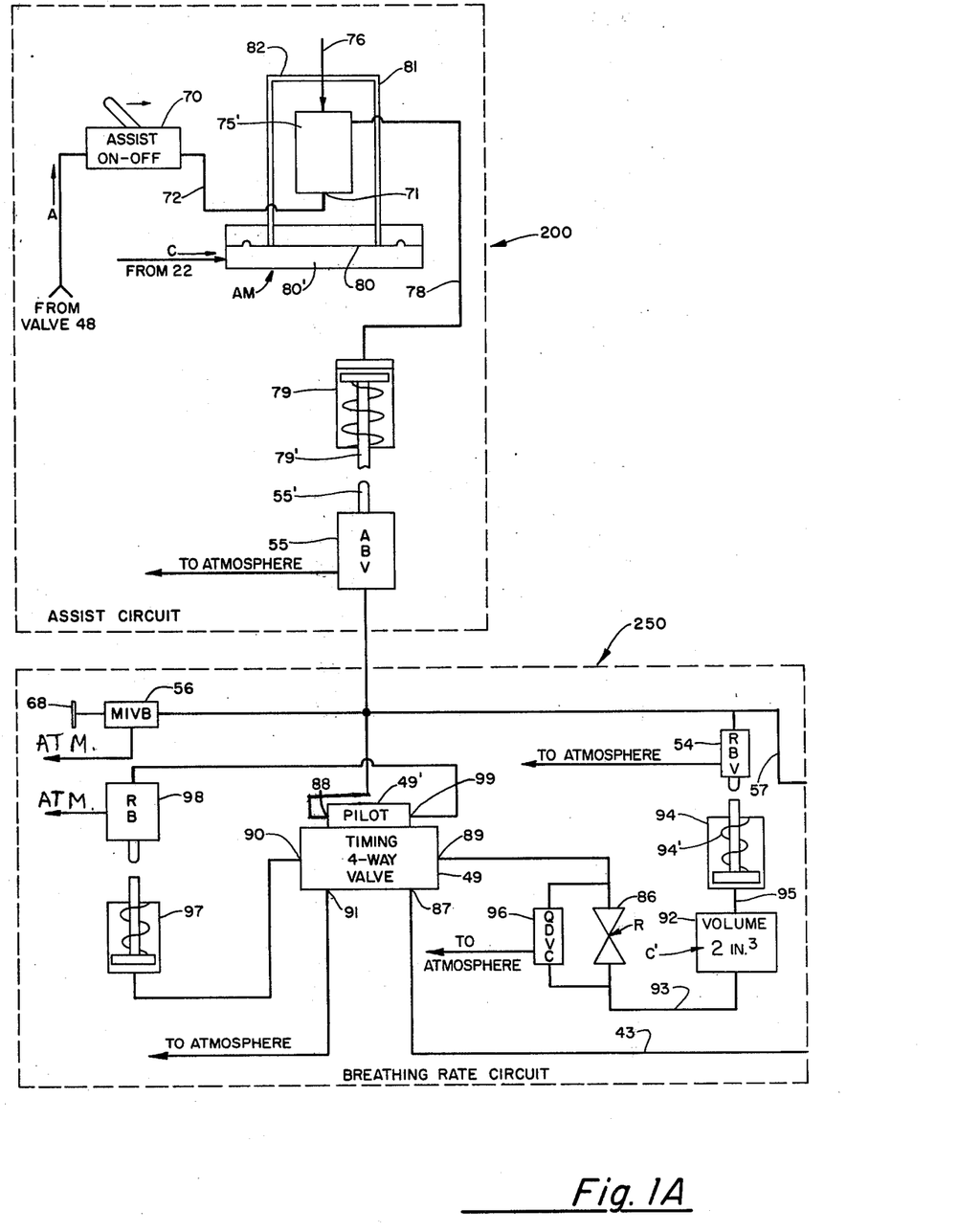
FIGS. 1A and 1B are schematic diagrams of the present invention, depicting its features and capabilities.
Figure 1B:
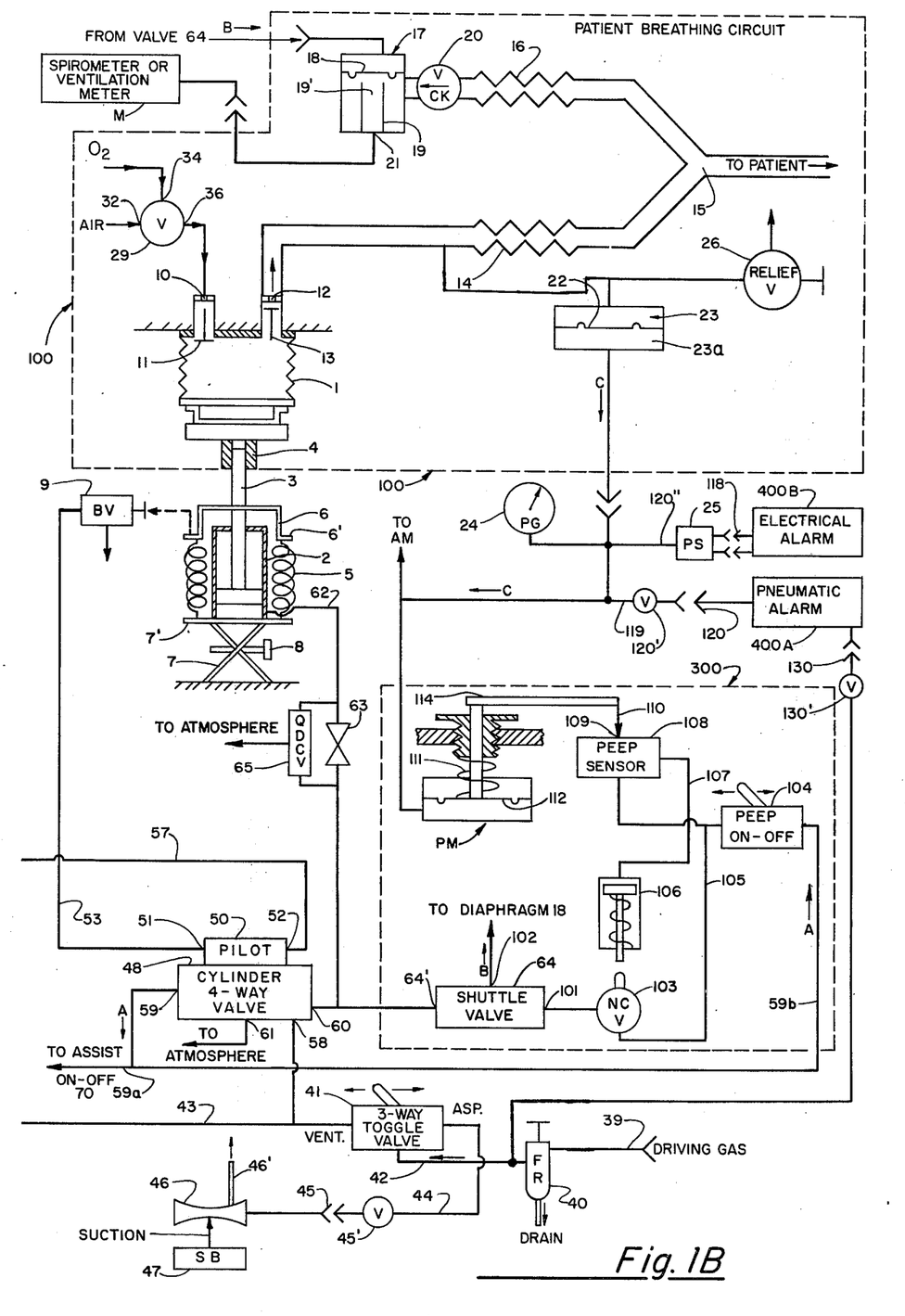

Referring now to the drawings wherein like reference characters designate like or corresponding parts throughout, there is illustrated in FIGS. 1A and 1B a diagram of a ventilator embodying the invention. The ventilator includes a variable volume ventilating gas reservoir in the form of a cylindrical bellows 1 driven axially by a piston 3 which moves within a pneumatically actuated driving cylinder 2. When the ventilator is used in a non-rebreathing mode, coupling 4 is used to connect the gas reservoir bellows 1 to the piston 3, but in a rebreathing circuit this coupling is omitted. Piston 3 is returned by means of return springs 5 which are held between a flange 6' of a cylinder cup 6 and an upper platform 7' of a scissor jack 7. A knob 8 of the scissor jack 7 serves as a volume setting means by controlling the elevation of the jack 7, hence controlling the elevation of the cylinder 2 and the precompression of the gas reservoir bellows 1 at the start of inspiration. With the jack platform 7' completely lowered the maximum stroke of the gas reservoir bellows 1 occurs; while with the jack platform 7' completely elevated, the gas reservoir bellows 1 is almost completely compressed axially allowing only a minimum stroke to occur. When the flange 6' of the cylinder cup 6 strikes the upper bleeder valve 9, pneumatic valving to be described later causes the springs 5 to return the piston 3 to its completely retracted position, in the cylinder 2.

Figure 3:
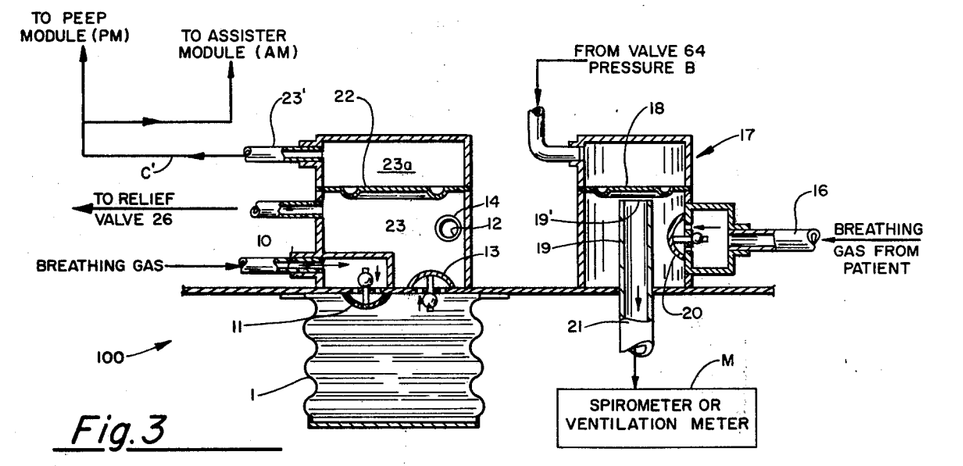
FIG. 3 is a vertical sectional view of a patient breathing circuit excluding the air-oxygen concentration valve.

The net effect is that the axial stroke of the gas reservoir bellows 1 is fixed, and it cycles at a predetermined rate to supply breathing gas to the patient via the removable, sterlizable patient circuit 100. Reference is now made to FIG. 3 which shows parts of a patient circuit 100 to better advantage.

When the gas reservoir bellows 1 is extended, breathing gas is drawn into an inlet port 10, through inlet valve 11 to fill the bellows 1. When the bellows 1 is compressed, the breathing gas is sealed from the inlet port 10 by the closing of the inlet valve 11 and the gas flows to the patient via an outlet valve 13, an outlet port 12, a corrugated hose 14 and a "Y" connection 15. Gas is kept from flowing into a hose 16 during inspiration by a pressure actuated exhaust valve 17. During inspiration gas pressure B from a shuttle valve 64 acts on a diaphram 18 sealing an opening 19' to a tube 19 effectively closing off the hose 16. On exhalation as the gas reservoir bellows 1 extends, the outlet valve 13 closes the port 12. Simultaneously, gas pressure B drops to zero as will hereinafter be more fully explained and the diaphram 18 no longer closes the tube 19. The exhaled gas in the hose 16 flows through a check valve 20, the tube 19 and out of a port 21. The volume of exhaust gas through the port 21 can be monitored by means of an external spirometer or ventilation meter M, to measure the amount of breathing gas used by the patient per given time interval.

It is to be noted that an isolation diaphram 22 causes the pressure in a chamber 23 which is connected to the hose 14 to be reflected into a chamber 23a while providing isolation. The pressure in the chamber 23a is measured by a ventilator system pressure gage 24, and applies to a pressure sensor 25, an assister module AM, and a PEEP module PM. A whistling type of spring loaded relief valve 26 is connected to the chamber 23 and to the hose 14 and the Y-fitting 15 and is manually adjustable by the operator. The valve 26 is set at a value to which the maximum pressure in the system is to be limited. The relief valve 26 is constructed so as to whistle when it is actuated to serve as an audible alarm signal to the operator that the patient is impeded and needs special care.

Figure 2:
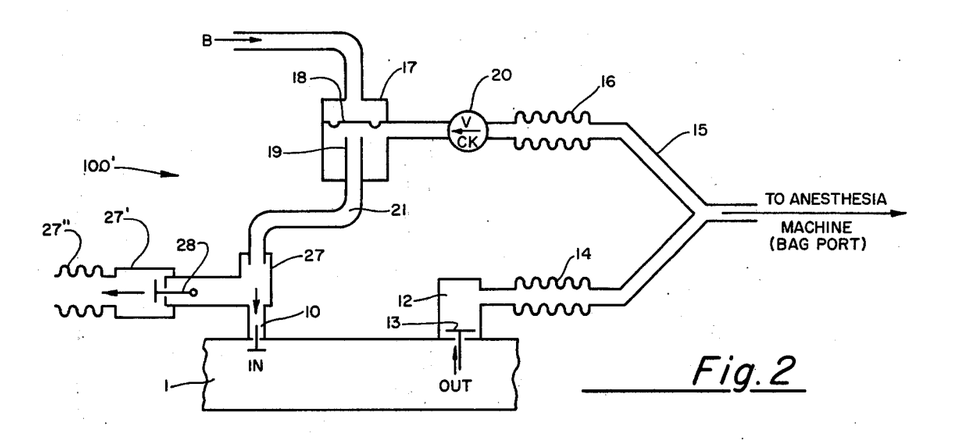
FIG. 2 is a schematic diagram of a patient breathing circuit with a spill valve for anesthesia use.

In the event that the circuit is to be used in a closed, rebreathing circuit in combination with an anesthesia machine, the patient circuit configuration 100' of FIG. 2 is employed. In this case, the outlet port 21 of the tube 19 is connected to the inlet port 10 by a connector 27 which contains a spill valve 28. On extension of the gas reservoir bellows 1, the spill valve 28 is sucked closed. Only if excess gas is led into the breathing circuit by the anesthesia machine is this gas "spilled" overboard to atmosphere, thereby preventing build-up of pressure within the bellows 1 and to the patient. It is desirable that the spill valve 28 be provided with an output port 27' so that the spilled gas can be led by suitable hose 27" outside of the operating theater so as not to affect the operating team. It is to be noted that during the rebreathing operation, the patient exhalation rate controls the rate of extension of the bellows 1, and not the rate of return of the piston 3 as during non-rebreathing operation. This is the reason why the coupling 4 is not employed during the rebreathing operation.

It is to be noted that the inlet port of the pressure actuated exhaust valve 17 is fitted with the check valve 20. This check valve serves a dual function. First it seals off the pressure actuated exhaust valve 17, if the patient creates a suction in the hoses 14 and 16 by demanding assistance, thereby increasing the sensitivity of the assist circuit by reducing its overall volume; second it serves as a safety means in the event the diaphram 18 accidentally develops a leak; by closing and preventing the high pressure gas "B" from entering the hose 16 and the Y-fitting 15 and from there acting on the patient. Gas from such a leak will exhaust through the port 21 during inspiration and would be detected by the spirometer or ventilation meter M. Normally gas only leaves the port 21 during exhalation by the patient.

Figure 4:
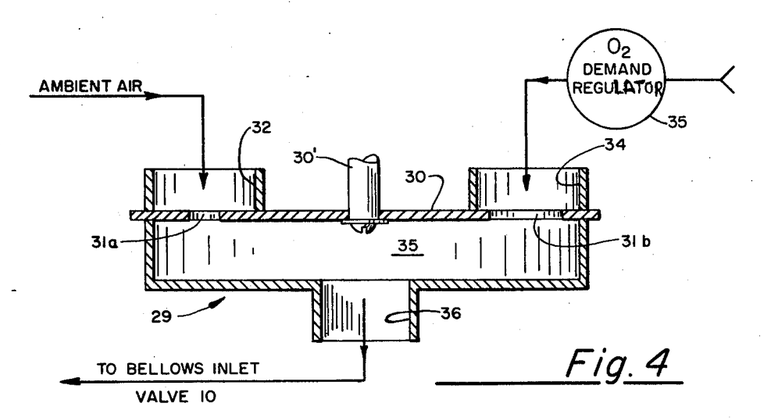
FIG. 4 is a vertical sectional view of the air-oxygen concentration valve for obtaining desired oxygen concentration.
Figures 5, 6, 7:
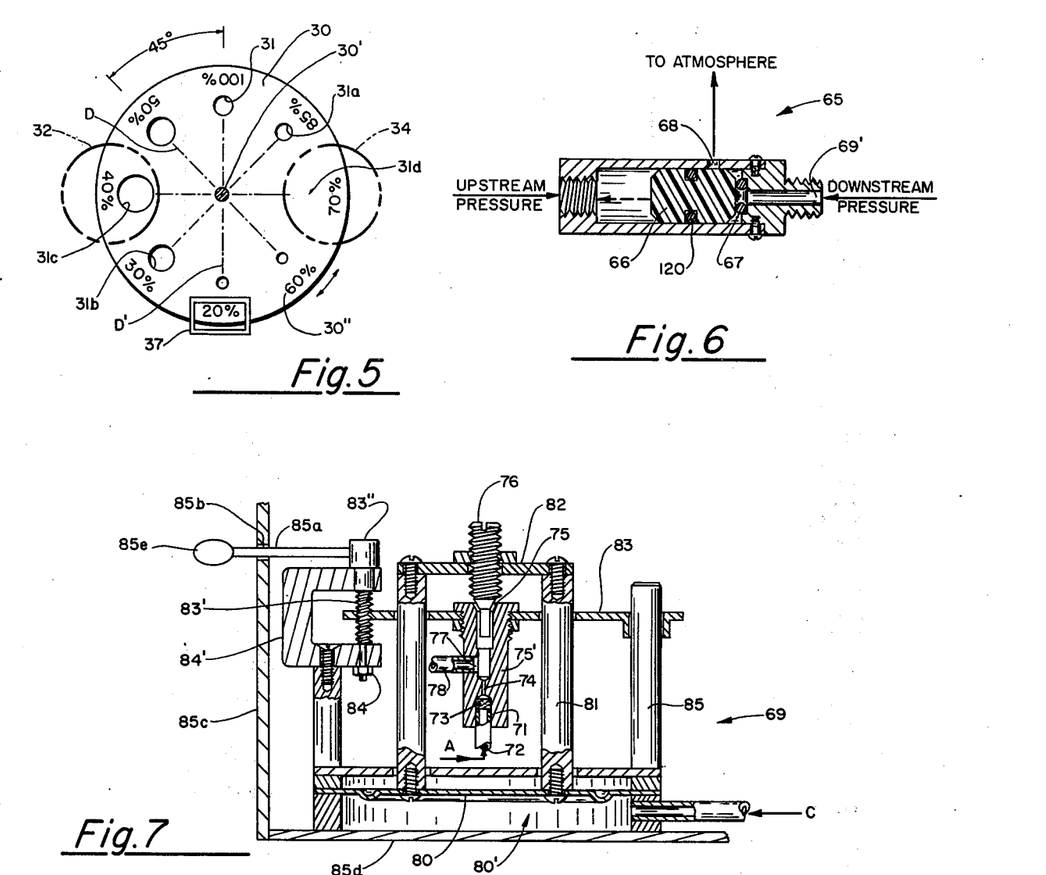
FIG. 5 is a plan view of the air-oxygen concentration valve disk, depicting orifice pairs.
FIG. 6 is an enlarged axial sectional view of a quick discharge check valve.
FIG. 7 is a vertical sectional view of a preferred assistor sensor circuit.

An air-oxygen valve 29 is connected to the inlet port 10 of the bellows 1 so that a pre-determined oxygen concentration may be dialed in. The air-oxygen valve 29 is shown in FIG. 4. The heart of this valve is a disk 30 which contains pairs of diametrically opposed orifices 31. One orifice 31a is shown located in an ambient air intake port 32, the other paired orifice 31b is located in an oxygen intake port 34. Oxygen from a pressurized source is supplied to this port from a conventional oxygen demand type regulator 35 which supplies oxygen only as the gas reservoir bellows 1 is extending. The amount of gas entering each port 32 and 34 is directly related to the size of the orifice located in each port. The gases mix in a mixing chamber 35 an exit through an output port 36 which is connected to the inlet port 10 of the gas reservoir 1. The disk 30 may be rotated on a shaft 30' to align different sized pairs of orifices in the inlet ports, thereby providing a different known oxygen concentration in the air-oxygen mixture filling the gas reservoir 1 and utlimately delivered to the patient. Details of the disk 30 are shown in FIG. 5. The disk contains four pairs of orifices 31, although in one case the orifice pair consists of a large hole 31c and no hole (a blank) at the diametrically opposite other end 31d. All orifices parts are located on diameters D spaced 45° apart and having a common center. The orifice in each pair are diametrically opposite each other. Immediately outboard of each orifice is engraved a concentration percentage 30" such as "20" which appears in a window 37 located at one end of the diameter D' connecting the pair of orifices then in place in the ports 32 and 34. In the concentration setting shown in FIG. 5 it can be seen that the largest orifice 31c is located in the ambient port 32 while the blank space 31d is located in the oxygen ports 34; and the window 37 bears the engraved legend "20" which designates 20% oxygen. Under this condition, the oxygen supply is blocked and ambient air is allowed to flow in freely. Since ambient air has a nominal concentration of 20% oxygen, the air-oxygen mixture in the gas reservoir 1, delivered to the patient is 20%. If the disk is rotated 180 degrees, the blank space 31d seals off all ambient air, the large orifice 31c permits unimpeded entrance of 100% oxygen from the pressurized source, and the window 37 shows the legend "100".

Rotating the disk at 45° intervals permits choice of pairs of orifices which line up with the intake ports. The legend in window 37 then bears the oxygen concentration in the breathing gas admitted to the gas reservoir 1. Hence it is possible to dial in a desired oxygen concentration; 20%, 30%, 40%, 50%, 60%, 70%, 85% and 100% with the disk 30 as shown in FIG. 5. Choice of relative sizes of orifice pairs drilled in the disk 30 permits the selection of any oxygen concentration between 20% (ambient air) and 100% (pressurized source) with a high degree of accuracy. The previous valves listed are considered oxygen concentration that are practical for ventilator use.

We now will consider the pneumatic circuit in FIG. 1B which is responsible for controlling the movement of the piston 3 within the pneumatic cylinder 2, and hence the movement of the gas reservoir 1. Pressured driving gas, which need not be of breathing quality enters a line 39 and is reduced in pressure to a predetermined ventilator pressure, such as 35 psig, by a filter-regulator (FR) 40, which in addition to establishing a standard system pressure, filters incoming gas and automatically removes all water so as to protect all valving in the pneumatic circuit. A three way valve 41 directs filtered driving gas in a line 42 to either a ventilator line 43 or to an aspirator line 44. The aspirator line 44 contains a quick connect fitting 45 which has incorporated a sealing valve 45' so that it is shut off in the event that nothing is plugged into the quick connect fitting. In the "aspirate" (ASP) position the ventilator is OFF while in the ventilate (VENT) position, the ventilator is ON so that the valve 41 serves as an ON-OFF valve. An aspirator consisting of a venturi 46 and a suction bottle (SB) 47 may be connected to the quick connect fitting 45 permitting suction via a standard medical catheter 46' to be applied to the patient to clear his airway. This is a required step in employing the ventilator as an emergency resuscitator.

With the valve 41 in the ventilate position the line 43 is pressurized and feeds a cylinder 4-way valve 48 and a timing 4-way valve 49. The 4-way valve 48 controls the direction of motion of the piston 3 within the pneumatic cylinder 2. It is equipped with a pilot section 50, which has two ports 51 and 52. An upper bleeder valve (BV) 9 is connected to the port 51 via a line 53. Similarly the port 52 has connected to it three bleeder valves i.e. a rate bleeder valve (RBV) 54, an assist bleeder valve (ABV) 55 and a manual inspirator bleeder valve (MIBV) 56 via a line 57. When the upper bleeder valve 9 is depressed upon being struck by the flange 6' of the cylinder cup 6, the pressure in the line 53 drops allowing a shuttle (not shown) located in the pilot 50 to shift, thereby shifting the 4-way valve 48 causing a pressure port 58 to be connected to a port 59 permitting driving gas A to be sent via lines 59a, 59b to an assist ON-OFF valve 70 and a PEEP ON-OFF valve 104. Simultaneously a port 60 of the 4-way valve 48 is connected to a port 61, which is open to atmosphere (ATM) and allows the pressure in a cylinder line 62 to fall and the return springs 5 to retract the piston 3 in the pneumatic cylinder 2. The return springs 5 are employed in lieu of driving gas on the rear of the piston 3 in order to conserve driving gas and to increase efficiency of the system. Piston 3 remains in retracted position until either the rate bleeder valve 54, the assist bleeder valve 55 or the manual bleeder valve 56 is actuated. If actuated, the pressure in the line 57 drops, permitting the pilot 50 to connected the pressure port 58 of the 4-way valve 48 to the port 60, and the port 59 to the exhaust port 61. Driving gas is then led via the line 62 to the pneumatic cylinder 2 driving the piston 3 upwardly. Simultaneously the lines 59a, 59b to the assist and PEEP valves 70, 104 are depressurized so that the assist and PEEP valves 70, 104 cannot be actuated during the inspiration stroke. The construction of the 4-way valve 48 and the associated bleeder valves 9, 54, 55 and 56, are described in detail in my previous U.S. Pat. No. 3,251,359.

During inspiration, piston 3 of the cylinder 2 is extended at a rate determined by a needle valve 63 which simultaneously determines how quickly the gas reservoir 1 is depressed and therefore the inspiratory flow rate of gas to the patient. The valve 63 therefore is a prime control, controlling the inspiratory flow rate. When the port 60 is pressurized, by actuation of either of the bleeder valves 54, 55 or 56, a shuttle valve 64 causes a pressure B to be generated to activate the diaphram 18 of the pressure actuated exhaust valve 17 to seal the tube 19, thereby causing all breathing gas to be delivered to the patient via the hose 14. The action of the shuttle valve 64 is described below in more detail. When inspiration ceases, the port 60 is depressurized, pressure B is also depressurized and the diaphram 18 opens the tube 19 of the pressure actuated exhaust valve 17, permitting the patient to exhale passively through the port 21, as previously described. When the bleeder valve 9 is struck, inspiration ceases, the piston 3 retracts in the cylinder 2 and the bellows 1 expands, refilling for the next inspiratory stroke, while the patient exhales.

It is essential that the piston 3 retracts rapidly within pneumatic cylinder 2 to permit rapid filling of gas bellows 1. This requirement is imposed by the necessity of having a filled reservoir at all times when the patient requests assistance or when the ventilator is operating in an "assist" mode. As described, the rate of retraction will be determined by the inspiratory rate needle valve 63, since the springs 5 must retract the piston 3 at a rate determined by how fast the driving gas previously admitted to the cylinder 2 during inspiration is forced through the port 60 (via the line 62 and needle valve 63) to the atmosphere port 61 of 4-way valve 48. To permit rapid movement of the piston 3, a quick discharge check valve 65 is placed in parallel with the needle valve 63. The construction of the quick discharge valve 65 is shown in FIG. 6. During inspiration, the upstream pressure at the valve port 60 is greater than the downstream pressure in the line 62 due to the pressure drop occuring as gas flows through the needle valve 63. Hence the shuttle 66 of quick discharge check valve 65 (shown in FIG. 6) is pressed against an "O"-ring 67 sealing off the downstream pressure line. When the upstream pressure drops to zero, the port 60 of the 4-way valve 48 is connected to the port 61 and the downstream pressure drives the shuttle 66 away from the O-ring 67, allowing downstream gas to quickly evacuate to the atmosphere via the port 68. The shuttle 66 is provided with an O-ring seal 120 to prevent leakage of gas thereabout. As soon as the port 60 is pressurized again, the shuttle 66 closes the downstream port 69'. The quick discharge check valve 65 is then sealed, thereby allowing the driving gas rate to be determined by the needle valve 63 as previously described. A similar quick discharge check valve 96 is also employed in the breathing rate timing circuit which will be described later.

Inspiration is initiated by actuation of the bleeder valves 54, 55 or 56. The simplest bleeder valve circuit is the bleeder 56 which is manually operated in the event the operator wishes to manually control the start of an inspiratory breath. Physically it is located at the ventilator's front panel. The valve 56 is provided with a push button 68 for light finger actuation.

The assist circuit 200 (FIG. 1B) draws driving gas power from the port 59 of the 4-way valve 48 only during the exhalation portion of each breathing cycle. Gas pressure "A" can be directed to an assist sensor 69 provided that a two-way toggle valve 70 is in the "ON" position. The assist sensor module 69 is shown best in FIG. 7. Gas enters the sensor 69 at a port 71, through a line 72. In the sensor 69, the gas is filtered by a filter 73 prior to entering an orifice 74, which serves to economize the amount of gas consumed by the sensor 69. Driving gas normally escapes through a vent 75, the annular space between a sensor body 75' and a needle 76. If the needle 76 is actuated by the patient requesting assistance, it seals off the vent 75 and the driving gas is forced out of a port 77 through a line 78 to an assist actuator 79. The assist actuator 79 is a miniature spring return pneumatic cylinder having a piston 79'. When the cylinder 79 is pressurized, the piston 79' extends striking an arm 55' of the bleeder 55 which initiates inspiration. The needle 76 is arranged to assist a diaphram 80 via two parallel posts 81 and a cross brace 82. An attempt by the patient to inhale causes a negative pressure C below the isolating diaphram 22, and the chamber 80', below the assist diaphram 80. Gas pressure C causes the needle 76 to be pulled into the sensor 69 blocking the vent port 75. The magnitude of the assist effort is controlled by the distance the needle 76 must be pulled to seal off the vent port 75. The sensor body 75' is mounted on a nut plate 83 (FIG. 7) which is engaged with a screw 83' which may be turned manually by the operator to a desired position to fix assistor sensitivity. Since the screw 83' may turn, but not advance, by reason of the screw head 83" and a bearing 84 on a C-arm 84', only the nut plate 83 may rise or descend. A guide rod 85 prevents the nut plate 83 from rotating. If the vent port 75 is very small the needle 76 is almost contracting the body 75', the assistor circuit will be very sensitive and an inspiration suction as low as 0.5cm H₂O will initiate inspiration. If the vent port is open i.e. the needle 76 separated from the body 75', progressively higher suction efforts on the part of the patient are required to initiate inspiration.

Screw 83' may be manually adjusted by moving a lever 85a connected to the screw head 83" and terminating outwardly in a handle 85e. The lever 85a extends outwardly through a slot 85b in a front panel 85c of the ventilator apparatus. The panel 85c is connected to a ventilator base 85d.

The breathing rate circuit determines how many breaths per minute are supplied to the patient if neither the manual bleeder valve 56 or the assist bleeder valve 55 are actuated. If either of the bleeder valves 54, 55, or 56 is actuated (as well as bleeder valve 54) a series of events occur which resets a breathing rate circuit 250 so that the next breath occurs after the passing of a given time interval. Thus if the breathing rate control 86 is set at twelve breaths per minute, the breathing rate bleeder valve 54 must be actuated once every five seconds, thereby causing inspiration to be initiated regularly once every five seconds. If the manual inspiration bleeder valve 56 or the assist bleeder valve 55 is actuated prior to the end of five seconds, then inspiration will start, and the next inspiration will automatically occur five seconds later, unless manual or assisted inspiration is initiated sooner. Typically, a breathing rate control 86 uses a needle valve calibrated to provide six to sixty breaths per minute in graduated intervals of two breaths per minute. It will be seen that the breathing rate is fixed by the time required to charge a fixed volume to a given pressure. The breathing rate is proportional to an R-C' time constant, where R is the resistance offered by the variable needle valve 86 and C' is the capacity of a fixed air volume container 92.

The heart of the breathing rate circuit 250 is the timing-4-way valve 49 which is identical in construction and operation to the 4-way valve 48 described in my U.S. Pat. No. 3,251,359 and there are common connections. The pressure line 43 is connected to a port 87 as well as the port 58. Also the bleeder line 57 is connected to a pilot port 88 and the port 52. Assume the port 87 is connected to a port 89, while a port 90 is depressurized, since it is connected to an atmospheric port 91. Driving gas enters the port 87, exits through the port 89 and flows at a rate determined by the setting of breathing rate needle valve 86 corresponding to the fixed volume of the container 92 connected to the valve 86 via a line 93. The container volume is typically fixed at 2 cubic inches. As the container 92 fills, the pressure rises in the rate actuator 94 which is connected to the container 92 via a line 95. The actuator 94 is similar to the actuator 79 in being a spring return miniature pneumatic cylinder. When the pressure rises sufficiently to compress an actuator spring 94' and further provides the force necessary to open the rate bleeder valve 54, then inspiration is initiated. Simultaneously, the loss in pressure at the pilot port 88 of the timing 4-way valve 49 causes the pilot 49' to shift and the valve 49 have the pressure port 87 connected to the port 90, and the port 89 to be connected to the atmospheric port 91. It will be noted that a quick discharge check valve 96 (similar to the valve 65 previously described) is in parallel with the breathing rate needle valve 86. When the pressure at the port 89 drops to atmospheric, the quick discharge check valve 96 quickly shifts, allowing an extremely rapid exhaust of the container 92, and the actuator 94, and the connecting of the tubes 93 and 95, in preparation for another timing cycle when the port 89 is again pressurized. Meanwhile, the port 90 has been pressurized, causing a reset actuator 97 to actuate a reset bleeder (RB) 98 reducing the pressure at a pilot port 99. This causes an almost instantaneous shift of the pilot 49' to occur, once again connecting the port 87 to the port 89, and the port 90 to the atmospheric port 91, thereby initiating once again timing gas flow through the bleeding rate needle valve 86, the container 92, and the rate actuator 94. The reset actuator 97 is depressurized and is ready to reset the timing valve 49 after the line 57 is depressurized by the actuation of either of the three bleeder valves 54, 55 or 56 connected to the line 57.

It will be noted that actuation of the rate bleeder valve 54 while the piston 3 of the pneumatic cylinder 2 is extending in inspiration has no effect since it signals an inspiration which is already in progress. However, the click of the rate bleeder valve 54 operating will be heard. For example, suppose the operator sets the controls carelessly so that the breathing rate is 60 times per minute, while the inspirator flow rate is such that it takes slightly less than two seconds to extend the piston 3, a click will be heard after one second while the piston 3 is extending to remind the operator he has inconsistent settings. The ventilator will continue to cycle, although at undesirable parameters until settings are corrected. This condition is far superior to that of having the ventilator stop cycling, which could be fatal to the patient.

It will also be noted that all the controls are independent. Thus the breathing rate control has no affect on inspiratory flow rate or volume setting, or vice versa. This enables an operator to dial in desired settings, and make instantaneous changes without the necessity of making repetitive adjustments of all knobs to obtain the desired parameters.

It has been found that some patients receive superior ventilation when subjected to a positive end expiratory pressure, i.e. when the starting and the end pressures during a breathing cycle are maintained above the zero level or atmospheric. This is equivalent to raising the entire pressure trace by a predetermined pressure valve (usually in the 0 to 20 CmH$_2$O range). In doing this it is desirable to translate the curve obtained at the zero level to the higher pressure level without changing the pressure trace waveform. The translation is conventionally accomplished by a Positive End Expiratory Pressure or PEEP valve which is placed directly in the patient breathing circuit. Usually it takes the form of a spring baised valve, having variable, adjustable bias, and which closes off the patient circuit exhalation port (preventing exhalation) below the bias setting and which opens the patient circuit exhalation port (allowing "free" exhalation) above the setting. Ideally it is desired that the valve should be full open or full closed, offering zero resistance when open and infinite resistance when closed so that there is no distortion introduced in the pressure trace. Actually, spring biased valves in series with the patient do cause distortion by throttling the "free" flow in a manner which adversely affects ventilation since exhalation of the patient is impeded (when compared to a zero level) rather than just shifted in the pressure axis. Furthermore, such a PEEP valve being loacted in the patient circuit is subject to contamination, and must be cleaned and sterilized between patients.

Figure 8:
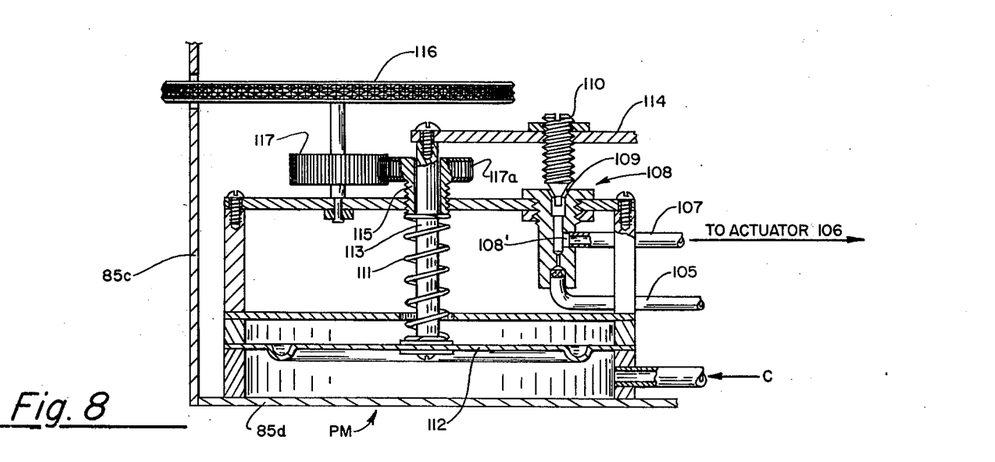
FIG. 8 is a vertical sectional view of a preferred PEEP (positive end expiratory pressure) circuit.

The PEEP circuit employed in the present ventilation system is novel and eliminates both objections by being (1) non-distorting and (2) located outside the patient circuit 100. The overall PEEP circuit 300 employed is shown in FIG. 1B, while the PEEP adjusting mechanism PM is depicted in FIG. 8. PEEP action is based on employing the pressure actuated exhaust valve 17 for a dual function. It will be recalled that this exhaust valve is closed during inspiration by means of the pressure B acting on the diapham 18, closing off the tube 19 and is open during exhalation when the pressure source B drops to zero. The PEEP circuit 300 operates so that the valve 17 is not pressurized during start of exhalation (wide open) and then it closes tightly when the exhalation pressure drops to the predetermined PEEP value so that the desired PEEP breathing is attained. This means that pressure "B" should be reinstated at a given patient pressure point at the end of exhalation. It will be noted that pressure "B" is the output of the shuttle valve 64. This shuttle valve has two pressure input ports 64', 101 and produces at an output port 102 the higher of the two pressure inputs while maintaining isolation between these two pressure sources. During patient inspiration, pressure exists at the port 60 of the 4-way valve 48 and hence at an input port 64' of the shuttle valve 64. The other input port 101 is not pressurized at this time, so that the pressure at the port 60 is also available at the output port 102 of the shuttle valve 64 and has been designated as pressure B. Normally, with PEEP during exhalation of the patient, the pressure at the port 60 (hence the port 64') is zero and there is zero pressure at the port 101, causing no output at port 102, and the exhaust valve 17 is wide open. The PEEP circuit is designed to provide a pressure at the port 101, only after the patient exhalation pressure drops to the positive end pressure desired, thereby causing pressure B to exist at the port 102, and closing the valve 17 to shut off exhalation. Once inhalation again commences, pressure at the port 101 drops to zero, but pressure at the port 64' is re-established thereby providing a pressure B to close off the exhaust port of the valve 17 during inhalation.

Pressure can exist at the port 101 of the shuttle valve 64 only if two conditions are met: (1) a normally closed valve 103 is actuated and (2) a pressure A is avaliable to this valve. It is to be noted that the pressure source B originates at the port 59 of the 4-way valve 48, only during exhalation. If a PEEP ON-OFF valve 104 is toggled to the ON position by the operator, pressure A is available to the valve 103 via a line 105. Further the valve 103 can only open if a PEEP actuator 106 (similar to the actuators 79, 94 and 97 previously described) is pressurized by gas in a line 107. A PEEP sensor 108 (similar to the assist sensor AM) is located between the lines 105 and 107. A vent port 109 of the sensor 108 is opened or shut by a needle 110; see FIG. 8. A spring 111 biases a PEEP diapham 112 in a downward direction. This bias is translated to the needle 110 by a rod 113 and a cross bar 114 to seal the vent port 109 of the sensor 108. Under this condition gas in the line 105' flows through the port 108', and the line 107 to actuate the normally closed valve 103 by the actuating cylinder 106 whereby pressure B from the shuttle valve 64 then closes the pressure actuated exhaust valve 17 as previously described. If a positive pressure C from the patient circuit 100 is greater than the spring bias on the diaphram 112 then the needle 110 opens the vent port 109 of the sensor 108 causing zero pressure to exist in the line 107 and there is no actuation of the actuator 106, and no output B from the shuttle valve 64; and thence the exhaust valve 17 is wide open. It can therefore be seen that at the end of the inspiration and start of exhalation when there is maximum pressure in the breathing circuit, this high pressure C overcomes the biased diaphram 112 and through the sequence just described maintains the valve 17 wide open. When the pressure C falls during exhalation to a positive value, the spring biased diaphram 112 prevails and causes the needle 110 to close the vent port 109 of the sensor 108, a sequence is established which results in closing the exhaust valve 17. The spring bias on the diaphragm 112 is manually adjusted by a screw 115 which is adjustable at the front panel 85c by a control knob 116, and gears 117, 117a. Increasing the spring bias by compressing the spring 111 causes the exhaust valve 17 to shut off at a higher patient pressure C, resulting in a pressure trace displaced by this high amount above the zero pressure axis. It will be noted that zero PEEP can be obtained by two means: (1) The PEEP ON-OFF valve 104 is placed in OFF position or (2) with the valve 104 ON, if the bias of spring 111 111 is reduced to so low a valve that even zero pressure C keeps the needle 110 up and the vent 109 open to prevent producing a pressure B during exhalation. In practice zero pressure will be a small positive pressure of sufficient magnitude to keep the needle 110 up. The PEEP setting knob 116 permits the operator to preset the spring bias to introduce a PEEP pressure in the 0-20 cm H$_2$O range. The PEEP setting can be confirmed by observing the pressure gauge 24 reading at start of inspiration. Zero PEEP is best obtained by the valve 104, and is most economical of driving gas since it prevents loss of gas through the vent port 109 of the sensor 108. Summarizing, it is important to note that the exhaust valve 17 is either fully open or closed, causing no distortion in Pressure Trace, as PEEP is introduced and that all critical PEEP controls are isolated from the patient circuit 100, and are not subject to patient contamination.

Figure 9:
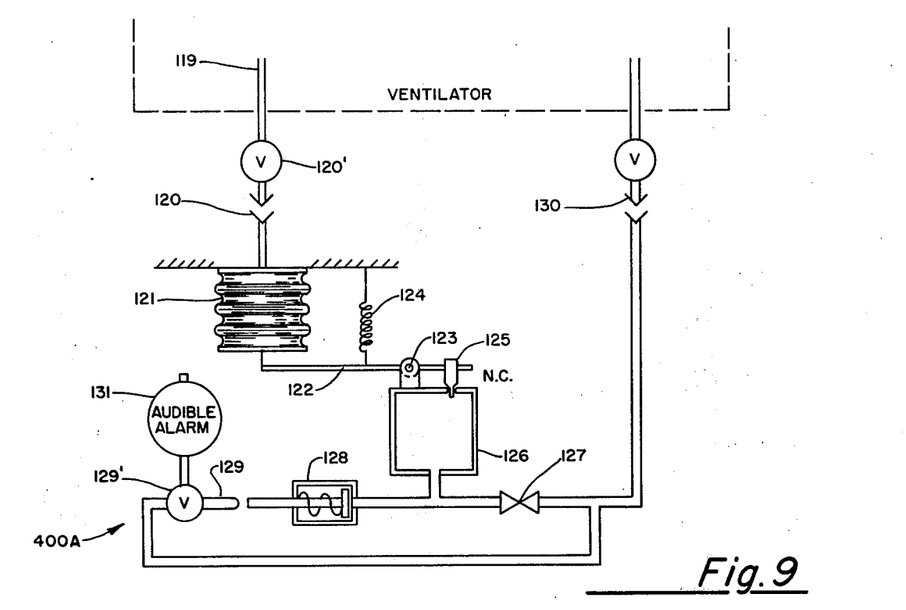
FIG. 9 is a schematic diagram of an all pneumatic alarm module or unit.
Figure 10:
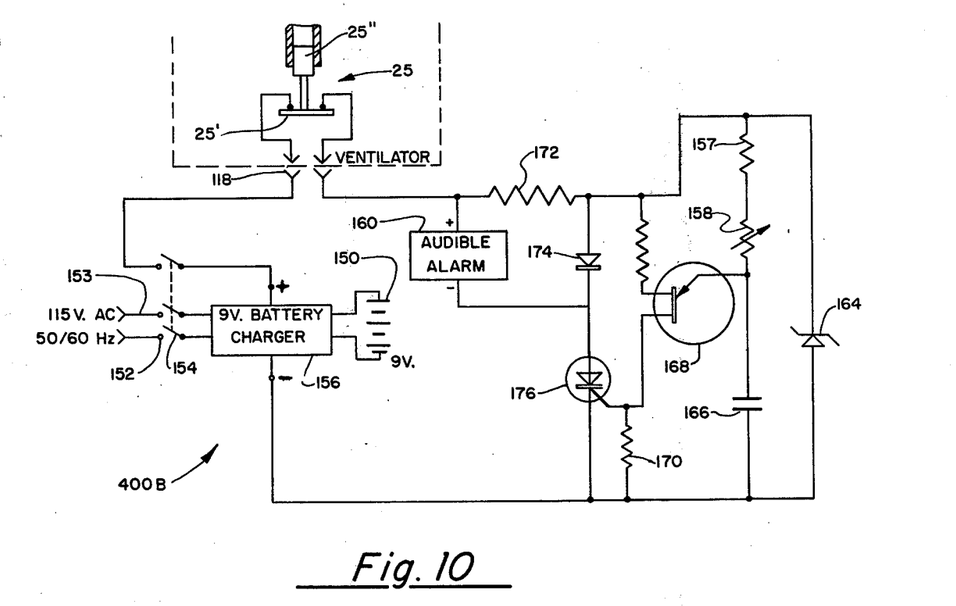
FIG. 10 is a schematic diagram of an electrical alarm module or unit.

The ventilator system is provided with a monitor alarm 400A or 400B to provide an audible alarm for alerting attending personnel in the event of ventilator failure or accidental disconnection of Y-fitting 15 to the patient. Alarm 400A is pneumatically operated. Alarm 400B is electrically operated.

FIG. 9 shows a pneumatic alarm module 400 A which can accompany the all pneumatic ventilator system. When the system is to be used in an emergency vehicle a pneumatically operated alarm module is preferred over an electrically operated alarm to avoid use of batteries and electronic parts. Referring now to FIGS. 1 and 9, a line 119 is connected in circuit with the isolation diaphram 22 and the chambers 23, 23a. A quick connect fitting permits attachment of the alarm module 400A to the ventilator system. When not attached the quick connect part of the fitting on the ventilator has a sealing valve 120' so that the line 119 is effectively sealed when the alarm module is not attached. Similarly a quick connect fitting 130 with a sealing valve 130' is used to provide driving gas from the ventilator to the alarm module. The alarm module has a pressure sensitive element such as a bellows 121 which will extend whenever the ventilator is cycling and a patient is connected. When the pressure exceeds a predetermined valve, such as 5 Cm H$_2$O pressure, the bellows 121 strikes a lever 122, overcoming a return spring 124, allowing it to pivot at a pin 123 and open a valve 125 in a volume 126. When the valve 125 is open, the volume 126 is vented to atmosphere. When the ventilator is not cycling, or insufficient pressure is generated due to the patient not being connected to the ventilator, the valve 125 is closed. Driving gas charges the volume 126 at a rate determined by the setting of a needle valve 127, provided the valve 125 is closed. The pressure in the charged volume 126 will actuate a miniature spring loaded actuator 128, to depress an arm 129 of the valve 129' to permit driving gas to enter a whistle 131 which acts as the audible alarm. The charging time for the volume 126 through the adjustable needle valve 127 can be set to occur in from 1 to 30 seconds by the operator using a calibrated control. If the valve 125 is never opened, the alarm 131 will sound at the end of the designated charging time. If however, the valve 125 is continually opened by the cycling and proper operation of the ventilator, the volume 126 will be exhausted before the pressure builds up to the alarm pressure level, and the alarm whistle 131 will not operate.

FIG. 10 shows an electrical alarm unit 400B which may be used with the ventilator in place of the alarm unit 400A for a hospital installation to alert hospital personnel in the event of a ventilator failure or an accidental disconnection of the Y-fitting to the patient. The pressure sensor 25 is subject to the pressure "C" since it is built into the ventilator body in the line 119. When the alarm module 400B is plugged into the electrical connector 118, information from this sensor is fed into the alarm circuit.

The pressure sensor 25 includes a normally closed pressure switch 25' with a plunger 25" which requires 5 Cm H$_2$O to open the switch 25' when the sensor 25 senses positive pressure within the ventilator gas reservoir bellows 1 on the inspiratory flow part of the cycle. Whenever the inspirator flow pressure exceeds the switch actuating pressure, the switch 25' opens, thereby interrupting electrical pulses that would normally trigger the monitor alarm. If these pulses are interrupted due to failure in producing positive ventilating pressures in bellows 1 or if the rate of producing such interruption falls below a preset valve, an audible alarm 160 will be triggered. The alarm is controlled by a manually set time delay control which can be set to delay the period before sounding, i.e. the range is from 1 to 30 seconds in a typical unit. The alarm and its associate circuit is housed within an accessory module which may be easily affixed to the basic ventilator. The alarm module is powered by an internal rechargeable battery 150. If electrical power is available at terminals 152, the module may be plugged in by closing a switch 154 during use, during which time the battery 150 will be trickle charged by a charger 156. The battery 150 will automatically supply power to the alarm unit in the event of failure of electrical power at the terminals 152. With unit 400B not plugged into the ventilator system, the internal battery 150 can be given a full charge by connecting a line cord 153 into an AC outlet and closing the power switch 154.

When the module is plugged into the ventilator connector 118, and the main power switch 154 is placed in the closed ON position, power from the battery 150 or from the electric lines through the battery charger 156 is provided to an RC timing circuit (to be hereinafter more fully described) if a pressure switch 25' in the sensor 25 is closed. If the ventilator is cycling normally and breathing gas pressure is being generated each breath due to the patient's being securely connected to the ventilator, then the switch 25' opens on pressure rise (inspiration) and power is cut off to the timing circuit components of the alarm module. Power is automatically restored on exhalation when the switch 25' normally closes, unless PEEP is employed. Assume the ventilator is not cycling, the switch 25' is normally closed and the operator places the power switch 154 in closed ON position, and sets a timing circuit variable resistor 158 to a setting of 10 seconds. After 10 seconds an alarm 160 will sound. If however the ventilator is turned on, a patient connected and a breathing pressure of over 5 Cm H₂O generated on each inspiration, with breathing rate set at 12 per minute, then there would be a pressure pulse opening the switch 25′ each five seconds and the timing circuit components would be reset to completely off each five seconds so that the alarm would not sound. If two cycles are missed the alarm 160 would sound. The circuit variable resistor 158 is calibrated and continuously adjustable from 1 to 30 seconds at the operator's option.

When power is applied to the timing circuit, a silicon controlled rectifier 176 is off and there is no voltage applied to the alarm 160. A timing capacitor 166 is charged through timing resistors 157, 158 until the voltage across the capacitor 166 reaches the peak voltage of a unijunction transistor 168 at which time the transistor 168 fires, generating a pulse across a resistor 170 which triggers the rectifier 176. The supply voltage minus the rectifier voltage drop appears across the alarm 160 causes an audible signal to be produced. Holding current for the rectifier 176 is provided through a resistor 172 and a diode 174. When the rectifier 176 triggers, the voltage across the transistor 168 drops to less than 2 volts due to the clamping action of the diode 174. This acts to rapidly set and maintain a low voltage on the capacitor 166, so that the time interval is maintained with acceptable accuracy. The time delay of the RC circuit depends on the time constant for charging the capacitor 166, and is the product of the sum of resistances of resistors 157, and 158 and the capacitance of the capacitor 166. Since the resistor 158 is variable the time constant can be varied so as to have any value in the 1 to 30 seconds range before the alarm 160 will sound. A zener diode 164, is used to regulate the direct current voltage to a constant value to assure constant action of the timer with changes in power supply voltage.

The electrical alarm module 400B described above is functionally equal to the alarm module 400A and while suitable for hospital use, has a disadvantage in that it requires an electrical power supply and introduces electronic and electrical components, particularly the internal battery 156 in an otherwise pneumatic system. When a portable ventilator system is used in emergency vehicles, it will be more desirable to provide an all pneumatic alarm module such as shown in FIG. 9 to accompany the all pneumatic ventilator system of FIG. 1.

The ventilator described above can be fabricated to offer ranges of adjustable parameters. For an adult unit, typical ranges would be:

| | |
|---|---|
| Bellows volume | 100 to 1600cc, continuously variable |
| Inspirator flow rate | 0.2 to 2.0 liter/sec., calibrated in 0.2 liter increments |
| Breathing rate | 6-60 per minute, in unit increments |
| Assistory sensitivity | −0.5 to −5 Cm H₂O pressure, continuously variable |
| Pressure limit | 20 to 80 Cm H₂O pressure, continuously variable |
| O₂ concentration | 20, 30, 40, 50, 60, 70, 85 and 100% directly dialed |
| PEEP setting | 0 to 20 Cm H₂O pressure, continuously variable |
| Alarm delay | 1 to 30 seconds, continuously variable in 1 sec increments |

By employing different size of ventilating gas reservoirs (such as pediatric unit having an adjustment range of 200 cc) the ventilator may be matched to different groups of individuals, infant, child or adult, and the desired ventilation parameters for each determined with a high degree of accuracy.

FIG. 1 depicts the preferred embodiment of the present invention. The ventilator shown in this figure may be used as either a controller or as an assister, in either a rebreathing or a non-breathing system. The operator decides whether the system is to be used as a controller, as a pure assister, or as an assister-controller, and whether or not control settings are made.

It should be understood that the foregoing relates to only a preferred embodiment of the invention, and that it is intended to cover all changes and modifications of the example of the invention herein chosen for the purposes of the disclosure, which do not constitute departures from the spirit and scope of the invention.

The invention claimed is:

1. A ventilator system for controlling, assisting, and monitoring a patient's breathing, comprising:

independent sources of air and oxygen;

controllable breathing gas mixing means connected to said sources for mixing air and oxygen in a selected proportion to constitute a breathing gas mixture;

a first hose means connected at one end to said breathing gas mixing means;

a bellows means connected to the other end of said first hose means for receiving said fresh breathing gas;

a second hose means having a first end connected to said bellows means and a second end adapted to be connected to; said patient for conducting said breathing gas to said patient;

a third hose means having one end connected to said second hose means between said first and second ends of said second hose means for receiving an exhaled gas from said patient;

an exhaust means having one end connected to the other end of said third hose means for conducting said exhaled gas from said third hose means;

a direct pressure transducer comprising a sealed rigid chamber connected at one end to said second hose means between said bellows means and said third hose means, said rigid chamber having a diaphragm means for sealing one portion thereof from a remaining portion of said rigid chamber whereby a pressure corresponding to the pressure of breathing gas in said second hose means is transferred through said transducer while isolating the breathing gas in said ventilator system;

a gage means connected to said remaining portion of said rigid chamber for measuring the pressure in said system; and a positive end expiratory pressure valve means operatively connected to said remaining portion of said rigid chamber to provide a passive non-resistant path for said exhaled breathing gas until exhalation gas pressure drops to a pre-determined magnitude, and then applying infinite resistance to gas flow in said path for providing a true shift of a reference pressure axis from zero value, to a selected pre-determined value, whereby monitoring of said patient's breathing may be performed without distortion of exhalation pressure and exhalation gas flow.

2. A ventilator system as defined in claim 1 wherein said system is used as a closed system, and further comprises a spill valve means having one end connected to said one end of said first hose means and said spill valve means having a second end connected to said other end of said exhaust means for spilling excess gas to atmosphere.

3. A ventilator system as defined in claim 1, further comprising a pneumatically operated alarm means connected to said remaining portion of said rigid chamber and responsive to breathing gas pressure therein to signal occurrences of abnormalities in breathing by said patient.

4. A ventilator system as defined in claim 1, further comprising:
   an axial reciprocable piston means detachably coupled to said bellows means for alternately compressing and expanding said bellows means;
   a source of driving gas;
   a pneumatic circuit means connecting said source of driving gas to said piston means for driving the same axially in one direction to compress said bellows; and
   means for driving said piston opposite to said one direction to expand said bellows, whereby breathing gas is delivered to said patient when said bellows is compressed and exhaled gas is received from said patient when said bellows is expanded.

5. A ventilator system as defined in claim 4, further comprising:
   an assist circuit means for assisting inhalation by said patient, comprising an assist sensor connected with said source of driving gas for receiving said driving gas during exhalation by said patient, and connected to said remaining portion of said rigid chamber for sensing a need by said patient; and
   an assistor actuator means connected between said assistor sensor and said piston means and arranged to initiate inhalation by said patient when actuated by said assistor sensor.

6. A ventilator system as defined in claim 4, further comprising manually operable valve means connected with said source of driving gas and said piston means for initiating inhalation by said patient at any time during a breathing cycle.

7. A ventilator system as defined in claim 4, further comprising a breathing rate circuit means for controlling the number of breaths per minute of said patient;
   comprising a gas container of fixed volume;
   an adjustable needle valve means connected with said source of driving gas and said gas container for controlling flow of driving gas into said container;
   a breathing rate actuator means connected with said container for actuation by driving gas when said container is filled; and
   a breathing rate valve means disposed for actuation by said breathing rate actuator means and connected with said piston means for maintaining inhalation by said patient at a rate determined by adjustment of said needle valve means.

8. A ventilator system as defined in claim 7, further comprising manually operable inhalation control valve means connected in pneumatic circuit with said source of driving gas and said piston means for initiating inhalation by said patient at any time during said breathing cycle and operative to deactivate said breathing rate circuit means during manual operation of said inhalation control valve means.

9. A ventilator system as defined in claim 8, further comprising assist circuit means for assisting inhalation by said patient comprising:
   an assistor sensor connected in pneumatic circuit with said source of driving gas for receiving said driving gas during exhalation by said patient, and connected to said remaining portion of said rigid chamber for sensing a need for inhalation by said patient; and
   an assistor actuator means connected in pneumatic circuit between said assist sensor and said piston means, arranged to initiate inhalation by said patient when actuated by said assist sensor, an operative to deactive said breathing rate circuit while assisting said patient's breathing.

* * * * *